United States Patent [19]

Cartmell et al.

[11] Patent Number: 5,484,434
[45] Date of Patent: Jan. 16, 1996

[54] ELECTROSURGICAL SCALPEL

[75] Inventors: Robert L. Cartmell, Bellbrook; Carl E. Goubeaux, Troy, both of Ohio

[73] Assignee: New Dimensions in Medicine, Inc., Dayton, Ohio

[21] Appl. No.: 162,782

[22] Filed: Dec. 6, 1993

[51] Int. Cl.⁶ .................................................. A61B 17/39
[52] U.S. Cl. ................................ 606/37; 606/39; 606/40; 606/42; 606/45
[58] Field of Search ........................ 606/32–34, 37–42, 606/45, 48–50

[56] References Cited

U.S. PATENT DOCUMENTS

| | | |
|---|---|---|
| 3,601,126 | 8/1971 | Estes . |
| 3,636,943 | 1/1972 | Balamuth . |
| 3,730,188 | 5/1973 | Ellman . |
| 4,161,950 | 7/1979 | Doss et al. . |
| 4,463,759 | 8/1984 | Garito et al. ............... 606/37 |
| 4,481,057 | 11/1984 | Beard . |
| 4,562,838 | 1/1986 | Walker ........................ 606/42 |
| 4,640,279 | 2/1987 | Beard . |
| 4,785,807 | 11/1988 | Blanch . |
| 4,802,476 | 2/1989 | Noerenberg et al. ........... 606/50 |
| 4,911,159 | 3/1990 | Johnson et al. ............... 606/37 |
| 5,055,100 | 10/1991 | Olsen ........................ 606/37 |
| 5,203,353 | 4/1993 | Easley et al. ................ 606/50 |
| 5,246,440 | 9/1993 | Van Noord ................... 606/39 |
| 5,290,285 | 3/1994 | Kirwan, Jr. .................. 606/50 |

*Primary Examiner*—Stephen C. Pellegrino
*Assistant Examiner*—Michael Peffley
*Attorney, Agent, or Firm*—Killworth, Gottman, Hagan & Schaeff

[57] ABSTRACT

A surgical scalpel for cutting the tissue of a patient and for selectively applying an electrosurgical cutting current or an electrosurgical coagulation current from an electrosurgical generator to the patient, includes a scalpel body defining a contoured external surface configured to be held comfortably in the hand of a surgeon, and an electrically conductive blade, mounted on and extending from the scalpel body, for cutting the tissue of a patient and for selectively applying electrosurgical cutting current or electrosurgical coagulation current to the tissue of a patient. The scalpel further includes a cable having an electrical connector for electrical connection to the electrosurgical generator, and manual switch means, mounted on the scalpel body, for controlling the application of electrosurgical cutting current and electrosurgical coagulation current to the tissue of a patient.

18 Claims, 4 Drawing Sheets

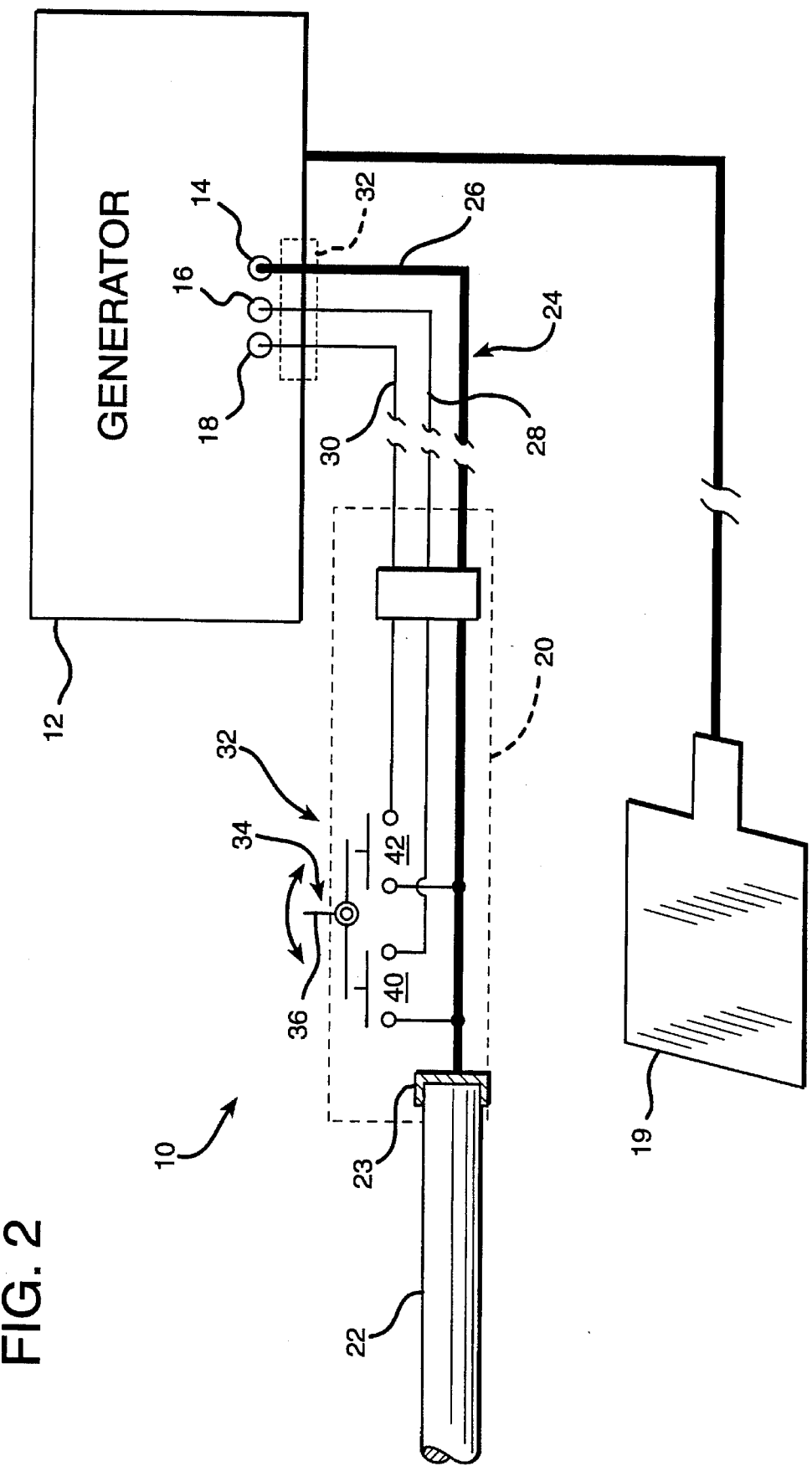

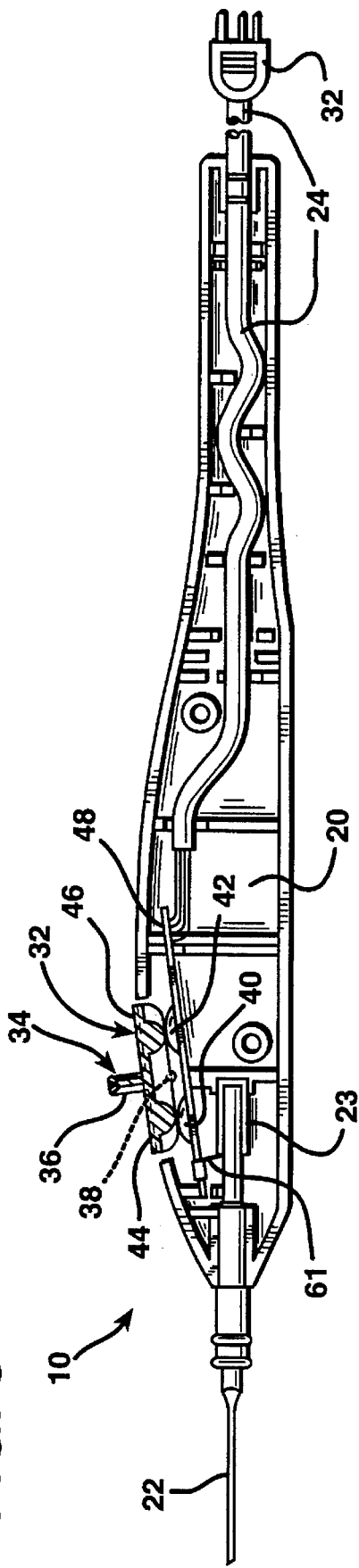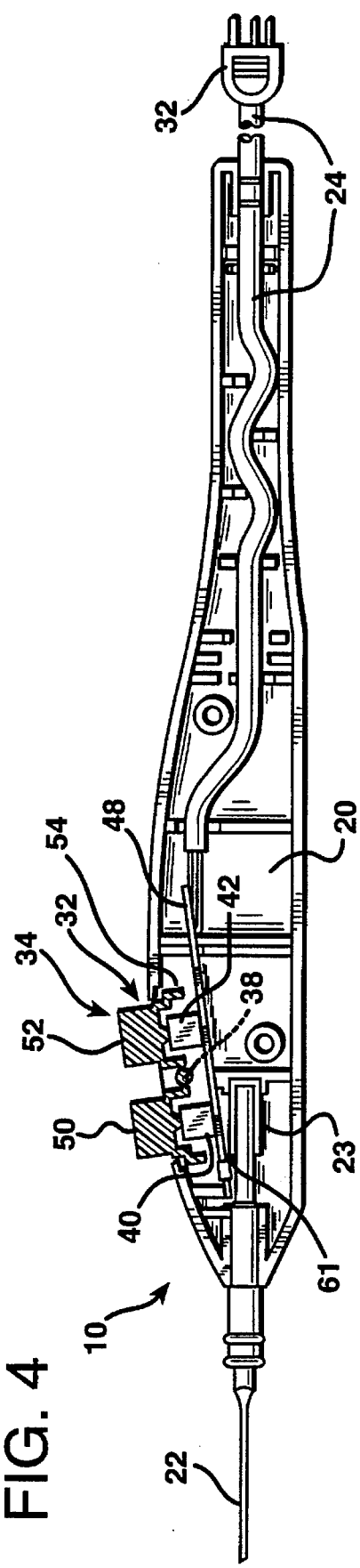

ELECTROSURGICAL SCALPEL

BACKGROUND OF THE INVENTION

The present invention relates to surgical scalpels and, more particularly, to a surgical scalpel in which an electrosurgical cutting current or an electrosurgical coagulation current can be applied to the tissue of a patient through an electrically conductive blade that is also used to effect cutting of the tissue.

Electrosurgery has become quite common for a number of reasons. Controlling bleeding during surgery is a significant problem, and it was found that coagulation, or hemostasis, could be accomplished by applying a radio frequency current to the affected patient tissue. Further, it was found that applying a radio frequency current to tissue through a scalpel facilitates the cutting action of the scalpel. Typically, an electric current is applied to the tissue of a patient via the scalpel at the same time that the scalpel is used to cut the tissue in a conventional manner. It is known that certain current wave shapes and frequencies enhance the cutting action of the electrosurgical scalpel, while other current wave shapes and frequencies tend to cause coagulation of blood in the region of an incision.

The electric current for electrosurgical procedures is provided by a generator including a radio frequency oscillator circuit. The electrosurgical current is applied to the patient by an active electrode connected to the generator by a cable, and is returned from the patient to the generator through a cable which is attached to a dispersive electrode. The dispersive electrode is secured to the patient's skin. The dispersive electrode is relatively large in area, thereby keeping the current density in the region of the dispersive electrode sufficiently low to avoid tissue burns.

Various approaches have been taken in the prior art to control the application of electrosurgical current to a patient. Commonly, a foot pedal switch has been used, with depression of the pedal resulting in either coagulation current or cutting current being supplied to the active electrode, such as shown in U.S. Pat. No. 4,640,279, issued Feb. 3, 1987, to Beard, and in U.W. patent No. 3,730,188, issued May 1, 1973, to Ellman. U.S. Pat. No. 3,601,126, issued Aug. 24, 1971, to Estes, also discloses the use of a foot pedal switch. Additionally, Estes suggests that a finger operated switch, mounted on the active electrode, may be used in lieu of a foot pedal switch.

Various single-use electrosurgical scalpels have included finger operated electrical controls. A common problem with such scalpels is reliability, since they have commonly incorporated snap switches that each consist of a snap metal dome having a peripheral edge lying on a printed circuit board land. Such a switch provides a connection to a second circuit board land when the central portion of the dome is snapped downward into contact with the second circuit board land. A problem associated with switches of this type is that the metal domes may oxidize over time, resulting in an undesired, high level of switch resistance. An additional problem is the cost associated with the manufacture of a disposable part having a great many separate components that must be carefully assembled. A further problem is that the movement of the surgeon's index finger in depressing a switch tends to cause the scalpel to pivot downward. This downward movement can be significantly amplified if the cutting blade is relatively long. Thus, switches of this sort have required care to insure that the scalpel blade is appropriately controlled.

Accordingly, it is seen that there is a need for an improved simple, reliable electrosurgical scalpel having a manually operated switch arrangement permitting the surgeon to supply electrosurgical cutting current or electrosurgical coagulation current to the electrically conductive scalpel blade.

SUMMARY OF THE INVENTION

This need is met by a surgical scalpel according to the present invention for cutting the tissue of a patient and for selectively applying an electrosurgical cutting current or an electrosurgical coagulation current from an electrosurgical generator to the patient. The electrosurgical generator has an electrical power terminal, a cutting switching terminal, and a coagulation switching terminal. The generator provides an electrosurgical cutting current at the electrical power terminal when the cutting switching terminal is electrically connected to the electrical power terminal, and an electrosurgical coagulation current at the electrical power terminal when the coagulation switching terminal is electrically connected to the electrical power terminal.

The scalpel comprises a scalpel body, an electrically conductive blade, mounted on and extending from the scalpel body, for cutting the tissue of a patient and for selectively applying electrosurgical cutting current or electrosurgical coagulation current to the tissue of a patient, and a cable for electrical connection to the electrosurgical generator. The cable includes an electrical power conductor connected at a first end of the cable to the electrically conductive blade, a cutting switching conductor, and a coagulation switching conductor. The cable further includes an electrical connector attached at a second end of the cable for electrically connecting the electrical power conductor to the electrical power terminal, for electrically connecting the cutting switching conductor to the cutting switching terminal, and for electrically connecting the coagulation switching conductor to the coagulation switching terminal. Finally, the scalpel includes manual switch means, mounted on the scalpel body and electrically connected to the electrical power conductor, the cutting switching conductor, and the coagulation switching conductor, for selectively connecting either the cutting switching conductor or the coagulation switching conductor to the electrical power conductor when it is desired to supply electrosurgical cutting current or electrosurgical coagulation current, respectively, to the electrically conductive blade.

The scalpel body comprises a molded plastic body defining a contoured external surface configured to be held comfortably in the hand of a surgeon. The scalpel body is generally elongated, with the electrically conductive blade extending from a first end of the scalpel body aligned with the longitudinal axis thereof. The cable extends from a second end of the scalpel body, opposite the first end.

The contoured external surface defines a thumb depression on one side of the scalpel body for engagement with the thumb of the hand of the surgeon, and a groove on the opposite side of the scalpel body, running perpendicular to the longitudinal axis of the body, for engagement with the second finger of the hand of the surgeon. If desired, the contoured external surface may define a depression on each side of the scalpel body for engagement with the thumb of the hand of the surgeon, and a groove on each side of the scalpel body, running perpendicular to the longitudinal axis of the body and positioned between the thumb depression and the blade, for engagement with the second finger of the hand of the surgeon, whereby the scalpel may be held by the surgeon comfortably in either hand.

The manual switch means includes finger actuator means, mounted on the scalpel body, for movement by the index finger of the hand of the surgeon from a neutral actuation position into either a cutting actuation position or a coagulation actuation position. The manual switch means may also include first and second switches, mounted in the scalpel body adjacent the finger actuator means. The first switch is electrically connected across the cutting switching conductor and the electrical power conductor for electrical connection therebetween when the finger actuator means is moved into the cutting actuation position. The second switch is electrically connected across the coagulation switching conductor and the electrical power conductor for electrical connection therebetween when the finger actuator means is moved into the coagulation actuation position.

The finger actuator means may comprise a pivot actuator member, mounted on the scalpel body, for pivotal movement from the neutral actuation position into the cutting actuation position or for pivotal movement from the neutral actuation position into the coagulation actuation position. Alternatively, the finger actuator means may comprise a first actuator button, mounted on the scalpel body for movement generally normal to the longitudinal axis of the scalpel body from the neutral actuation position into the cutting actuation position, and a second actuator button, mounted on the scalpel body for movement generally normal to the longitudinal axis of the scalpel body from the neutral actuation position into the coagulation actuation position.

The first and second switches may each comprise a sealed switch. A circuit board, mounted in the scalpel body, may support the first and second switches, with the switches being soldered to the circuit board. Alternatively, the first and second switches each comprises a membrane switch.

The electrical power conductor may be substantially heavier than either the cutting switching conductor, or the coagulation switching conductor. As a result, the electrical power conductor is capable of carrying the electrosurgical cutting current or the electrosurgical coagulation current, but at the same time the cable is flexible due to the reduced size of the switching conductors.

Accordingly, it is an object of the present invention to provide an improved surgical scalpel for cutting the tissue of a patient, and for selectively applying electrosurgical current to the patient, in which manual control of the application of the electrosurgical current is facilitated; to provide such an improved surgical scalpel in which the body of the scalpel is contoured to fit the hand of the surgeon; to provide such an improved surgical scalpel in which the electrosurgical current is controlled by a pair of switches actuated by either buttons or a pivotally mounted switch actuator; and to provide such an improved surgical scalpel in which a multi-conductor cable supplies electrosurgical current from an electrosurgical generator to the scalpel, and the electrical power conductor in the cable is substantially larger than the switching conductors in the cable.

Other objects and advantages of the invention will be apparent from the following description, the accompanying drawings and the appended claims.

BRIEF DESCRIPTION OF THE DRAWINGS

FIG. 2 is a schematic representation of the electrical circuitry associated with the electrosurgical scalpel of the present invention;

FIG. 3 is a view of the first embodiment of the electrosurgical scalpel, with half of the scalpel body removed to reveal interior components;

FIG. 4 is a view, similar to FIG. 3, of a second embodiment of the electrosurgical scalpel;

DETAILED DESCRIPTION OF THE PREFERRED EMBODIMENTS

Figure 1:
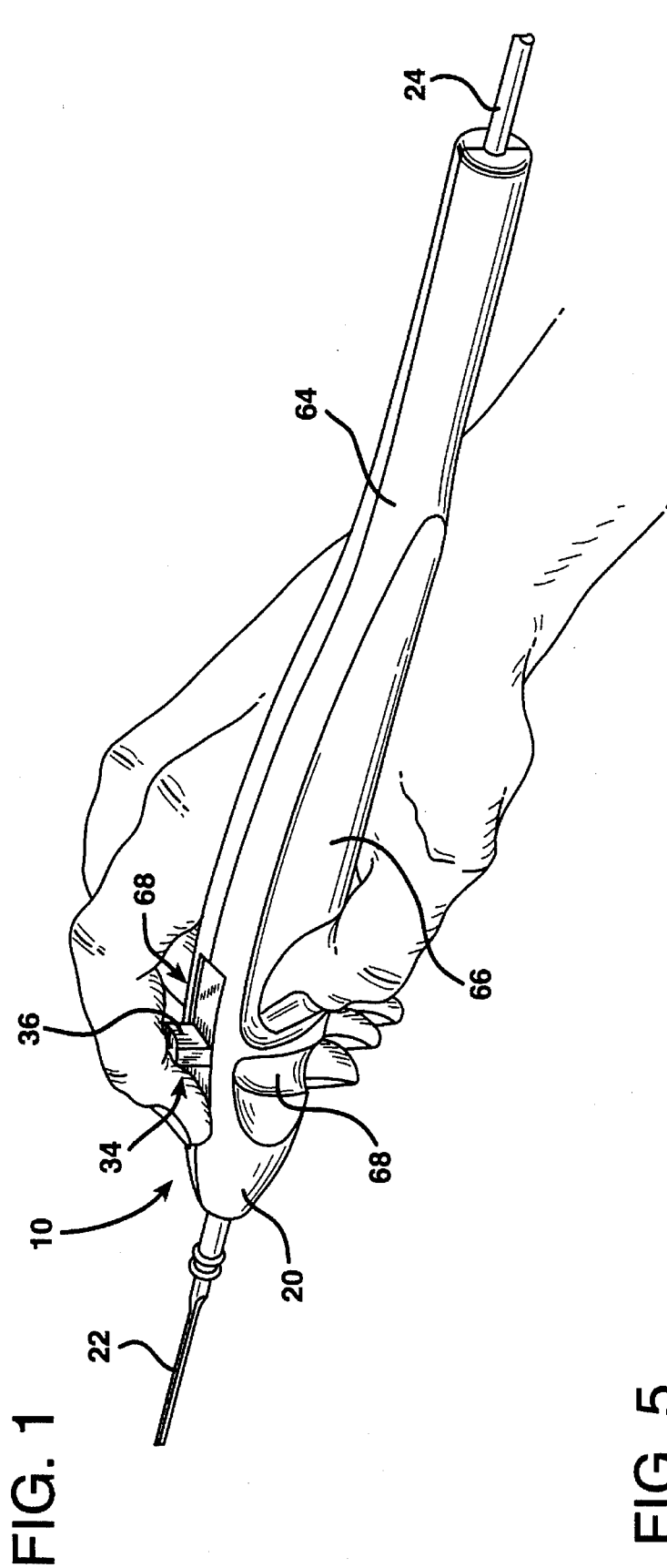
FIG. 1 is a perspective view of a first embodiment of the electrosurgical scalpel of the present invention for cutting the tissue of a patient and for selectively applying an electrosurgical cutting current or an electrosurgical coagulation current from an electrosurgical generator.
Figure 3A:
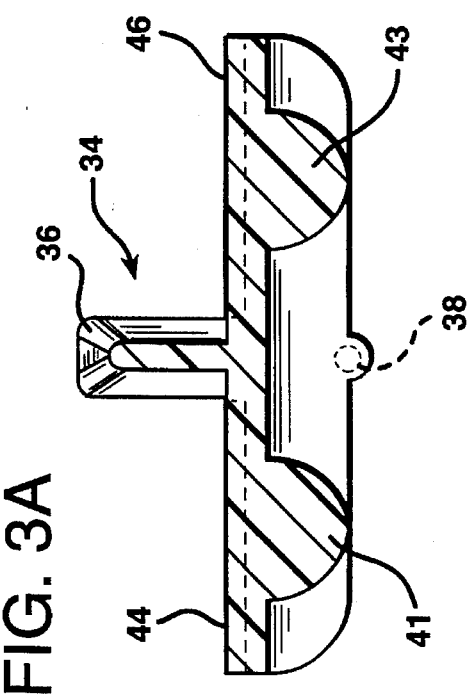
FIG. 3A is an enlarged sectional view of the finger actuator means of the embodiment of FIG. 3, taken generally along the line 3A—3A in FIG. 3B.
Figure 3B:
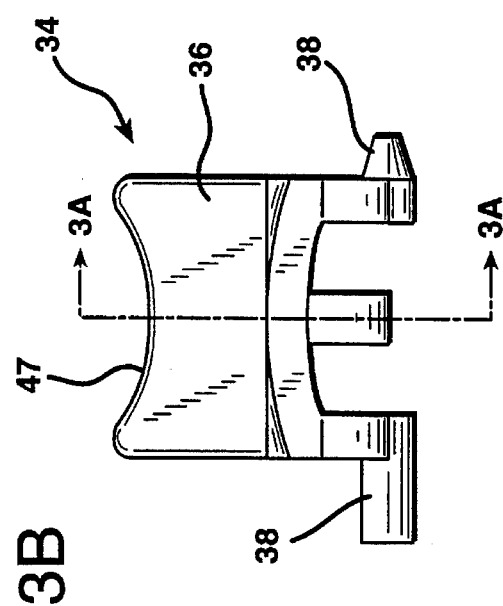
FIG. 3B is an end view of the finger actuator means as seen looking left to right in FIG. 3A.

FIGS. 1–3 illustrate a surgical scalpel 10 constructed in accordance with a first embodiment of the present invention. The scalpel 10 is used by a surgeon to cut the tissue of a patient and to apply selectively an electrosurgical cutting current or an electrosurgical coagulation current from an electrosurgical generator 12. The electrosurgical generator 12 has an electrical power terminal 14, a cutting switching terminal 16, and a coagulation switching terminal 18. Generator 12 may be any one of a number of commercially available electrosurgical generators. All such generators produce an electrosurgical cutting current at the electrical power terminal 14 when the cutting switching terminal 16 is electrically connected to the electrical power terminal 14. Further, such generators produce an electrosurgical coagulation current at the electrical power terminal 14 when the coagulation switching terminal 18 is electrically connected to the electrical power terminal 14. The electrosurgical current applied to the patient via the scalpel 10 is returned to the generator 12 through a dispersive electrode 19. Electrode 19 is typically applied to the skin of the patient in an area remote from the operation site, and is sufficiently large such that the density of the electrosurgical current exiting the body in the region of electrode 19 is not sufficient to cause tissue injury.

The scalpel 10 includes a scalpel body 20, which is preferably made of a molded plastic material. The scalpel body 20 includes right and left molded halves which are secured together by a snap arrangement, by an adhesive, or by sonic welding. Mounted on and extending from the scalpel body 20 is an electrically conductive blade 22. Blade 22 is secured in electrically conductive collar 23 and is utilized both to cut tissue and to apply selectively an electrosurgical cutting current or and electrosurgical coagulation current to the tissue.

A cable 24 provides an electrical connection to the electrosurgical generator 12. The cable 24 includes an electrical power conductor 26 connected ultimately at a first end of the cable to the electrically conductive blade 22 via collar 23, a cutting switching conductor 28, and a coagulation switching conductor 30. The cable 24 further includes an electrical connector 32, attached at a second end of the cable 24, for electrically connecting the electrical power conductor 26 to the electrical power terminal 14, for electrically connecting the cutting switching conductor 28 to the cutting switching terminal 16, and for electrically connecting the coagulation switching conductor 30 to the coagulation switching terminal 18.

A manual switch means 32 is mounted on the scalpel body 20 and is electrically connected to the electrical power conductor 24, the cutting switching conductor 28, and the coagulation switching conductor 30, for selectively connecting either the cutting switching conductor or the coagulation switching conductor to the electrical power conductor when it is desired to supply electrosurgical cutting current or electrosurgical coagulation current, respectively, to the electrically conductive blade 22 from the electrosurgical generator 12 via the electrical power conductor 24.

The manual switch means 32 is configured to permit the surgeon to switch on either a cutting current or a coagulation current with ease and to apply such currents through the blade 22. The manual switch means includes a finger actuator means 34, mounted on the scalpel body 20, for movement by the index finger of the hand of the surgeon from a neutral actuation position into either a cutting actuation position or a coagulation actuation position. In the first embodiment of the invention depicted in FIGS. 1–3, 3A, and 3B, the finger actuator means 34 comprises a pivot actuator member 36 which is mounted on the scalpel body 20 for pivotal movement from the neutral actuation position into the cutting actuation position or the coagulation actuation position. The pivot actuator member 36 is pivotally mounted by pin elements 38 which are received in recesses (not shown) in opposing halves of the scalpel body 20.

First and second switches 40 and 42 are mounted in the scalpel body adjacent the finger actuator means 34. The first switch 40 is electrically connected across the cutting switching conductor 28 and the electrical power conductor 26 for electrical connection therebetween when the finger actuator means 34 is moved into the cutting actuation position and pressure is applied to switch 40 by raised portion 41 of finger actuator means 24. Similarly, the second switch 42 is electrically connected across the coagulation switching conductor 30 and the electrical power conductor 26 for electrical connection therebetween when the finger actuator means 34 is moved into the coagulation actuation position and pressure is applied to switch 42 by raised portion 43 of finger actuator means 34. Pivoting pivot actuator member 36 forward causes the first switch 40 to be closed as arm 44 and portion 41 press down on switch 40. Similarly, pivoting pivot actuator member 36 rearward causes the second switch 42 to be closed as arm 46 and portion 43 press down on switch 42.

Switches 40 and 42 are shown as membrane switches, but it will be appreciated that other types of electrical switches may be used, as well, as discussed more fully below. The switches 40 and 42 are mounted on a circuit board 48 that is positioned in the scalpel body 20 for supporting the first and second switches. This arrangement simplifies the manufacturing process and results in reliable scalpel operation.

As best seen in FIG. 1, the index finger of the hand of the surgeon will typically rest on top of the end of the pivot actuator member 36. As a consequence, the pivot actuator member 36 has a curved end 47 (FIG. 3B) to make the position shown in FIG. 1 more comfortable. It will be appreciated that the movement of the index finger in actuating the scalpel for cutting or coagulation will be in a direction generally parallel to the longitudinal axis of the scalpel. As a consequence, any movement of the scalpel that this might cause would also be parallel to the longitudinal axis of the scalpel. Movement in this direction is not amplified by the length of the scalpel blade as would be the case with pivotal movement of the scalpel that would result from pressing control buttons on the scalpel body.

Reference is made to FIGS. 4, 4A, 4B and 5, which illustrate a second embodiment of the present invention, and in which elements corresponding to those in the first embodiment are labeled with the same reference numerals. In this embodiment, the finger actuator means 34, mounted on the scalpel body by pins 38, comprises a first actuator button 50 for movement in a direction generally normal to the longitudinal axis of the scalpel body 20, from the neutral actuation position shown in FIG. 4, downward into the cutting actuation position in which switch 40 is actuated. The finger actuator means 34 further includes a second actuator button 52 for movement generally normal to the longitudinal axis of the scalpel body 20 from the neutral actuation position shown in FIG. 4 into the coagulation actuation position in which switch 42 is actuated.

Buttons 50 and 52, shown in cross-section, may preferably be molded from a single piece 54 of relatively soft, flexible plastic. Piece 54 defines marginal shoulders which engage scalpel body 20. Adjacent the pins 38 are areas 55 of significantly reduced thickness. These areas comprise grooves which run across the width of piece 54 and cause it to be flexible, acting in the manner of a hinge. As a consequence either button 50 or 52 may be moved downward, independently of the other, into contact with switches 40 and 42, respectively.

Figure 5:
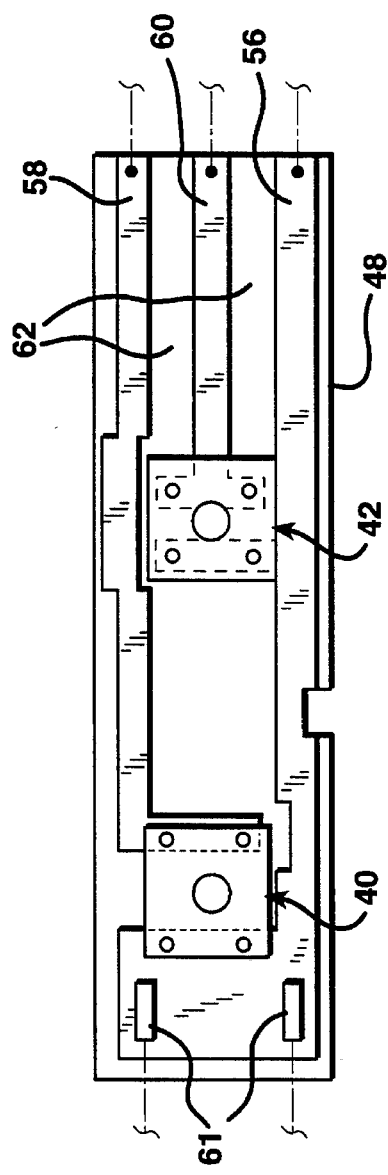
FIG. 5 is a diagrammatic view showing the circuit board and switch mounting arrangement for the second embodiment, as seen looking from above in FIG. 4.
Figure 4A:
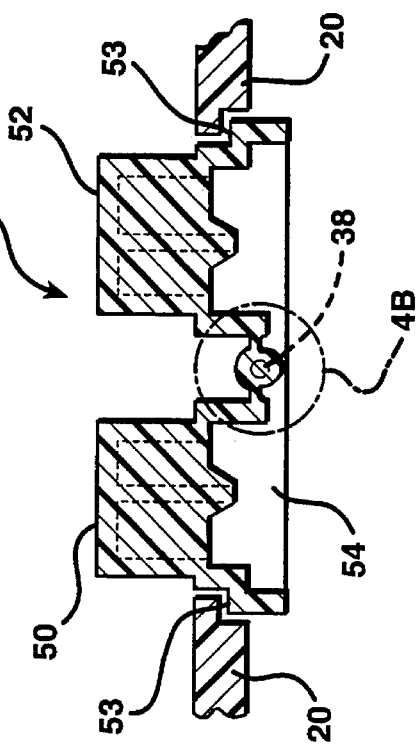
FIG. 4A is an enlarged sectional view of the finger actuator means of the embodiment of FIG. 4.
Figure 4B:
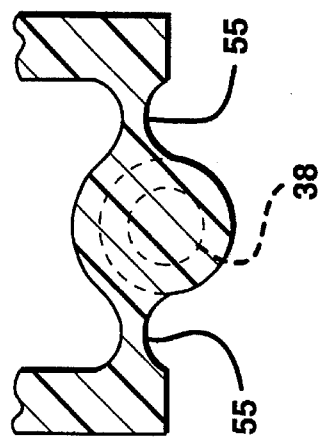
FIG. 4B is an enlarged sectional view of a portion 4B of the finger actuator means of FIG. 4A.

Switches 40 and 42 are shown as sealed, force-responsive PC switches of the type which make an electrical connection when a force is applied and which open the electrical connection when the force is removed. Such switches, intended for printed circuit board mounting, are available from any one of a number of sources, such as for example switch part number EVQ-PAG04K, available from Panasonic. Switches 40 and 42 are mounted on printed circuit board 48 which, in turn, is mounted in scalpel body 20. As shown in FIG. 5, switches 40 and 42 may preferably be soldered to the circuit board 48.

In order to facilitate the use of the surgical scalpel and, particularly, in order to reduce or eliminate interference in the manipulation of the scalpel which would otherwise result from a relatively stiff power cord, the individual conductors 26, 28, and 30 are sized to carry only the anticipated levels of current. As a result, conductors 28 and 30 are sized to carry 15 ma. of electrical current, while conductor 26 is sized to carry 1 amp. of electrical current. To accomplish this, conductor 26 may be made of #24 10 strand copper wire, while conductors 28 and 30 are made of #28 10 strand copper wire. The result is a cable 24 which is extremely flexible so that it does not interfere with movement of the scalpel, yet capable of carrying expected current loads.

The circuit board 48 includes copper lands 56, 58, and 60 which electrically connect with electrical power conductor 26, cutting switching conductor 28, and coagulation switching conductor 30, respectively. The lands 56, 58, and 60 are spaced sufficiently far apart on the circuit board 48 in the areas 62 such that the impedance between them is maintained high. The lands are sized in a manner similar to the individual conductors in cable 24. Copper land 56 is sized to carry one ampere, whereas lands 58 and 60 are sized to carry 15 ma. Copper land 56 is electrically connected to electrically conductive collar 23 by connector 61 attached at the forward end of circuit board 48. The conductors 26, 28, and 30 may be soldered to lands 26, 28, and 30, respectively, or alternatively, a connector may be utilized to provide a fast, reliable connection between the conductors and the lands.

Referring again to FIG. 1, it can be seen that the scalpel body 20 defines a contoured external surface 64 configured to be held comfortably in the hand of a surgeon. The scalpel body 20 is generally elongated, with the electrically conductive blade 22 extending from a first end of the scalpel body 20 and aligned with the longitudinal axis thereof. The cable 24 extends from a second end of the scalpel body 20, opposite the first end. The contoured external surface defines a thumb depression 66 on one side of the scalpel body 20 for engagement with the thumb of the hand of the surgeon, and a groove 68 on the opposite side of the scalpel body, running perpendicular to the longitudinal axis of the body 20, for engagement with the second finger of the hand of the surgeon.

In order to make the scalpel usable by both right handed and left handed surgeons, the contoured external surface 64 of the scalpel body defines a depression 66 on each side of the scalpel body for engagement with the thumb of either the right or the left hand of the surgeon. Further, a groove 68 is provided on each side of the scalpel body 20, running perpendicular to the longitudinal axis of the body 20 and positioned between the thumb depression 66 and the blade 22, for engagement with the second finger of either the right or the left hand of the surgeon. By this arrangement, the scalpel of the present invention may be held comfortably by the surgeon in either hand.

Having described the invention in detail and by reference to the preferred embodiments thereof, it will be apparent that other modifications and variations are possible without departing from the scope of the invention defined in the appended claims.

What is claimed is:

1. A surgical scalpel for cutting the tissue of a patient and for selectively applying an electrosurgical cutting current or an electrosurgical coagulation current from an electrosurgical generator to the patient, said electrosurgical generator having an electrical power terminal, a cutting switching terminal, and a coagulation switching terminal, said generator providing an electrosurgical cutting current at said electrical power terminal when said cutting switching terminal is electrically connected to said electrical power terminal, and said generator further providing an electrosurgical coagulation current at said electrical power terminal when said coagulation switching terminal is electrically connected to said electrical power terminal, comprising:

a scalpel body with a contoured external surface configured to be held comfortably in the hand of a surgeon, said contoured external surface defining a thumb depression on one side of the scalpel body operatively adapted to receive the thumb of the hand of the surgeon therein, and a finger groove on the opposite side of the scalpel body, running generally perpendicular to the longitudinal axis of the body, operatively adapted to receive the second finger of the hand of the surgeon therein, an electrically conductive blade, mounted on and extending from said scalpel body, for cutting the tissue of a patient and for selectively applying electrosurgical cutting current or electrosurgical coagulation current to the tissue of a patient, a cable for electrical connection to the electrosurgical generator, said cable including an electrical power conductor connected at a first end of said cable to said electrically conductive blade, a cutting switching conductor, and a coagulation switching conductor, said cable further including an electrical connector attached at a second end of said cable for electrically connecting said electrical power conductor to said electrical power terminal, for electrically connecting said cutting switching conductor to said cutting switching terminal, and for electrically connecting said coagulation switching conductor to said coagulation switching terminal, and manual switch means, mounted on said scalpel body and electrically connected to said electrical power conductor, said cutting switching conductor, and said coagulation switching conductor, for selectively connecting either said cutting switching conductor or said coagulation switching conductor to said electrical power conductor when it is desired to supply electrosurgical cutting current or electrosurgical coagulation current, respectively, to said electrically conductive blade from said electrosurgical generator via said electrical power conductor.

2. The surgical scalpel of claim 1, in which said scalpel body comprises a molded plastic body.

3. The surgical scalpel of claim 1, in which said scalpel body is generally elongated, with said electrically conductive blade extending from a first end of the scalpel body aligned with the longitudinal axis thereof, and said cable extends from a second end of the scalpel body, opposite said first end.

4. The surgical scalpel of claim 1, in which said contoured external surface defines a depression on each side of the scalpel body for engagement with the thumb of the hand of the surgeon, and a groove on each side of the scalpel body, running generally perpendicular to the longitudinal axis of the body and positioned between the thumb depression and said blade, for engagement with the second finger of the hand of the surgeon, whereby the scalpel may be held by the surgeon comfortably in either hand.

5. The surgical scalpel of claim 1, in which said manual switch means comprises:

finger actuator means, mounted on said scalpel body, for movement by the index finger of the hand of the surgeon from a neutral actuation position into either a cutting actuation position or a coagulation actuation position, and first and second switches, mounted in said scalpel body adjacent said finger actuator means, said first switch electrically connected across said cutting switching conductor and said electrical power conductor for electrical connection therebetween when said finger actuator means is moved into said cutting actuation position, and said second switch electrically connected across said coagulation switching conductor and said electrical power conductor for electrical connection therebetween when said finger actuator means is moved into said coagulation actuation position.

6. The surgical scalpel of claim 5, in which said finger actuator means comprises a pivot actuator member, mounted on said scalpel body for pivotal movement from said neutral actuation position into said cutting actuation position or said coagulation actuation position.

7. The surgical scalpel of claim 5, in which said finger actuator means is moved in a direction generally parallel to the longitudinal axis of the scalpel body into either said cutting actuation position or said coagulation actuation position.

8. The surgical scalpel of claim 5, in which said finger actuator means comprises a first actuator button, mounted on said scalpel body for movement generally normal to the longitudinal axis of said scalpel body from said neutral actuation position into said cutting actuation position, and a second actuator button, mounted on said scalpel body for movement generally normal to the longitudinal axis of said scalpel body from said neutral actuation position into said coagulation actuation position.

9. The surgical scalpel of claim 5, in which first and second switches each comprises a sealed switch.

10. The surgical scalpel of claim 9, further comprising a circuit board mounted in said scalpel body for supporting said first and second switches, said switches being soldered to said circuit board.

11. The surgical scalpel of claim 5, in which said first and second switches each comprises a membrane switch.

12. The surgical scalpel of claim 11, further comprising a circuit board mounted in said scalpel body for supporting said first and second switches.

13. The surgical scalpel of claim 5, further comprising a circuit board mounted in said scalpel body for supporting said first and second switches.

14. The surgical scalpel of claim 5, in which said electrical power conductor is substantially heavier than said cutting switching conductor, and in which said electrical power conductor is substantially heavier than said coagulation switching conductor, whereby said electrical power conductor is capable of carrying said electrosurgical cutting current or said electrosurgical coagulation current and said cable is flexible.

15. A surgical scalpel for cutting the tissue of a patient and for selectively applying an electrosurgical cutting current or an electrosurgical coagulation current from an electrosurgical generator to the patient, comprising:

a scalpel body defining a contoured external surface configured to be held comfortably in the hand of a surgeon, said contoured external surface defining a thumb depression on one side of the scalpel body operatively adapted to receive the thumb of the hand of the surgeon therein, and a finger groove on the opposite side of the scalpel body, running generally perpendicular to the longitudinal axis of the body, operatively adapted to receive the second finger of the hand of the surgeon therein, an electrically conductive blade, mounted on and extending from said scalpel body, for cutting the tissue of a patient and for selectively applying electrosurgical cutting current or electrosurgical coagulation current to the tissue of a patient, a cable including an electrical connector for electrical connection from said blade to said electrosurgical generator, and manual switch means, mounted on said scalpel body and electrically interconnected to said cable for controlling the application of electrosurgical cutting current and electrosurgical coagulation current to the tissue of a patient through said blade.

16. The surgical scalpel of claim 15, in which said scalpel body comprises a molded plastic body.

17. The surgical scalpel of claim 15, in which said scalpel body is generally elongated, with said electrically conductive blade extending from a first end of the scalpel body aligned with the longitudinal axis thereof, and said cable extends from a second end of the scalpel body, opposite said first end.

18. The surgical scalpel of claim 15, in which said contoured external surface defines a depression on each side of the scalpel body for engagement with the thumb of the hand of the surgeon, and a groove on each side of the scalpel body, running generally perpendicular to the longitudinal axis of the body and positioned between the thumb depression and said blade, for engagement with the second finger of the hand of the surgeon, whereby the scalpel may be held by the surgeon comfortably in either hand.

* * * * *